(12) United States Patent
Ito

(10) Patent No.: US 7,346,204 B2
(45) Date of Patent: Mar. 18, 2008

(54) METHOD OF AND APPARATUS FOR GENERATING PHASE CONTRAST IMAGE

(75) Inventor: Wataru Ito, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 493 days.

(21) Appl. No.: 10/144,836

(22) Filed: May 15, 2002

(65) Prior Publication Data

US 2002/0176615 A1    Nov. 28, 2002

(30) Foreign Application Priority Data

May 16, 2001 (JP) ............................. 2001-146138

(51) Int. Cl.
*G06K 9/00* (2006.01)
(52) U.S. Cl. .................... 382/132; 382/295; 382/298
(58) Field of Classification Search ........ 382/128–134, 382/293–295, 298; 378/62, 98.9–98.12, 378/43, 181, 55
See application file for complete search history.

(56) References Cited

U.S. PATENT DOCUMENTS

| | | | | |
|---|---|---|---|---|
| 5,881,126 A | * | 3/1999 | Momose | ...................... 378/36 |
| 5,982,953 A | * | 11/1999 | Yanagita et al. | ............. 382/294 |
| 6,226,353 B1 | * | 5/2001 | Wilkins et al. | ............ 378/98.9 |
| 2001/0038707 A1 | * | 11/2001 | Ohara | ........................ 382/132 |

FOREIGN PATENT DOCUMENTS

JP    2000-245721    9/2000

OTHER PUBLICATIONS

Hard x-ray phase imaging using simple propagation of a coherent synchrotron radiation beam, 1999.
Quantitative aspects of coherent hard X-ray imaging: Talbot images and holographic reconstruction, 1997.

* cited by examiner

*Primary Examiner*—Matthew C. Bella
*Assistant Examiner*—Shefali Goradia (Patel)
(74) *Attorney, Agent, or Firm*—Sughrue Mion, PLLC

(57) ABSTRACT

A phase contrast image is generated on the basis of a plurality of radiation images of an object taken in imaging positions which are different from each other in the distance from the object. An enlargement/reduction processing is carried out on the radiation images as taken in the imaging positions according to the distances between the imaging positions so that the radiation images become substantially the same in their sizes, and a phase contrast image is generated on the basis of the radiation images thus processed.

45 Claims, 8 Drawing Sheets

METHOD OF AND APPARATUS FOR GENERATING PHASE CONTRAST IMAGE

BACKGROUND OF THE INVENTION

1. Field of the Invention

This invention relates to a method of and an apparatus for taking a plurality of radiation images at different distances from the object and generating a phase contrast image on the basis of the radiation images obtained.

2. Description of the Related Art

There has been known a radiation image reproduction system in which an object is exposed to a radiation (X-rays, α-rays, β-rays, electron beams, ultraviolet rays or the like), the radiation passing through the object is detected by the use of, for instance, a stimulable phosphor sheet (to be described later) or a radiation detector panel (to be described later), thereby obtaining a radiation image data representing a radiation image of the object, and a radiation image is reproduced on the basis of the radiation image data after it is variously processed.

When certain kinds of phosphor are exposed to a radiation (X-rays, α-rays, β-rays, electron beams, ultraviolet rays), they store a part of energy of the radiation. Then when the phosphor which has been exposed to the radiation is exposed to stimulating rays such as visible light, light is emitted from the phosphor in proportion to the stored energy of the radiation. A phosphor exhibiting such properties is generally referred to as "a stimulable phosphor". In this specification, the light emitted from the stimulable phosphor upon stimulation thereof will be referred to as "stimulated emission". Further, a recording sheet comprising a layer of such a stimulable phosphor is referred to as "a stimulable phosphor sheet". When the stimulable phosphor sheet is used, the stimulable phosphor sheet is exposed to stimulating light after exposed to a radiation passing through an object and the stimulated emission emitted from the stimulable phosphor sheet upon exposure to the stimulating light is photoelectrically read, thereby obtaining image data representing a radiation image of the object. The radiation detector panel comprises a plurality of two-dimensionally arranged detecting elements and the detecting elements generates electric signals proportional to the amount of radiation projected onto the panel. Image data representing a radiation image of the object is obtained on the basis of the electric signals output from the detecting elements.

The radiation image thus obtained represents difference in intensity of the radiation passing through the object. For example, when the object includes a bone and a soft tissue, the radiation passing through the bone is largely attenuated and a very small part of the radiation reaches the detector (e.g., a stimulable phosphor sheet or a radiation detector panel) whereas the radiation passing through the soft tissue is less attenuated and a relatively large part of the radiation reaches the detector. Accordingly, in the case of such an object, the bone is expressed in white and the soft tissue is expressed in black. That is, a radiation image obtained is large in contrast and rich in information.

However, when the object mainly includes only soft tissues like a mammogram, difference in radiation attenuation by tissues is not so large, and accordingly, a radiation image obtained is small in contrast and poor in information.

In order to overcome this problem, there has been proposed a phase contrast imaging in which phase difference of radiation generated when the radiation passes through the object is visualized. The phase contrast imaging is based on the fact that when radiation is projected onto different materials, the phase of the wave of the radiation changes before and after passing through the materials and a phase difference is generated due to difference in propagation in the materials since radiation is an electromagnetic wave like light. When the object is of a soft part, a fine difference in tissues included in the soft part can be more clearly visualized by the phase contrast imaging since the phase difference is larger than the difference in attenuation. The phase contrast imaging is described in detail, for instance, in "Quantitative aspects of coherent hard X-ray imaging: Talbot images and holographic reconstruction" by Peter Cloetens, et al., (Proc, SPIE, Vol. 3154(1997), 72-82) (will be referred to as "paper 1", hereinbelow), and "Hard x-ray phase imaging using simple propagation of a coherent synchrotron radiation beam" by Peter Cloetens, et al., J. Phys. D:Appl. Phys.32(1999), A145-A151 (will be referred to as "paper 2", hereinbelow). According to these papers, a phase contrast image can be generated by taking images at a plurality of distances from the object by the use of a two-dimensional sensor (e.g., a radiation detector panel), thereby obtaining a plurality of pieces of image data representing a plurality of radiation images, and carrying out operation based on a predetermined algorithm by the use of the plurality of pieces of image data.

When taking a radiation image, the amount of radiation impinging upon a two-dimensional detector changes in inverse proportion to the square of the distance between the radiation source and the detector. Further sine the radiation is emitted from the radiation source to diverge away from the radiation source, the size of the radiation image as detected by the two-dimensional detector increases as the distance between the detector and the radiation source increases. Accordingly, there have been proposed radiation image taking apparatuses in which the gain at which the radiation image is read is controlled according to the distance between the object and the two-dimensional detector or the rate of enlargement is obtained. See, for instance, Japanese Unexamined Patent Publication No. 2000-245721.

The radiation projected onto the object in the phase contrast imaging is slightly divergent though it is substantially parallel light and accordingly, the sizes of the radiation images become slightly larger as the distance from the object increases. Accordingly, when a phase contrast image is generated on the basis of the images as taken in different imaging positions, position shift occurs due to mismatch of the sizes of the radiation images, which results in errors in the phase contrast image.

The amount of radiation impinging upon a two-dimensional detector is reduced as the distance from the object increases. Further, in the case, where a plurality of radiation images are obtained with a plurality of two-dimensional detectors disposed in a plurality of imaging positions, the amount of radiation impinging upon a two-dimensional detector is reduced also depending upon the number of detectors which the radiation passes through before impinging upon the detector. Accordingly, when a phase contrast image is generated on the basis of the images as taken in different imaging positions, it becomes difficult to precisely generate a phase contrast image due to mismatch of densities of the radiation images.

SUMMARY OF THE INVENTION

In view of the foregoing observations and description, the primary object of the present invention is to provide a method of and apparatus for precisely generating a phase contrast image.

In accordance with a first aspect of the present invention, there is provided a method of generating a phase contrast image on the basis of a plurality of radiation images of an object taken in imaging positions which are different from each other in the distance from the object, wherein the improvement comprises that an enlargement/reduction processing is carried out on the radiation images as taken in the imaging positions according to the distances between the imaging positions so that the radiation images become substantially the same in their sizes, and the phase contrast image is generated on the basis of the radiation images thus processed.

A density correction processing may be carried out, in addition to the enlargement/reduction processing, on the radiation images as taken in the imaging positions according to the distances between the imaging positions so that the radiation images become substantially the same in their densities, and the phase contrast image is generated on the basis of the radiation images thus processed.

The expression "the radiation images are substantially the same in their densities" as used here means, for instance, that the densities as represented by the average or the intermediate value of the pixel values of the radiation images, the peak signal value of the histogram of the image data representing the radiation images, or the like (will be simply referred to as "the average or the like", hereinbelow) are the same. Accordingly, the "density correction processing" is a processing to shift the pixel values of the radiation images by adding or subtracting a certain value to or from the pixel values of the radiation images so that the "averages or the like" of the pixel values of all the radiation images become substantially equal to each other.

The order in which the enlargement/reduction processing and the density correction processing are performed need not be limited.

In accordance with a second aspect of the present invention, there is provided a method of generating a phase contrast image on the basis of a plurality of radiation images of an object taken in imaging positions which are different from each other in the distance from the object, wherein the improvement comprises that a density correction processing is carried out on the radiation images as taken in the imaging positions according to the distances between the imaging positions so that the radiation images become substantially the same in their densities, and the phase contrast image is generated on the basis of the radiation images thus processed.

In accordance with a third aspect of the present invention, there is provided an apparatus for generating a phase contrast image on the basis of a plurality of radiation images of an object taken in imaging positions which are different from each other in the distance from the object, wherein the improvement comprises an enlargement/reduction processing means which carries out an enlargement/reduction processing on the radiation images as taken in the imaging positions according to the distances between the imaging positions so that the radiation images become substantially the same in their sizes, and an arithmetic means which generates the phase contrast image on the basis of the radiation images thus processed.

The apparatus may further comprise a density correction processing means which carries out a density correction processing, in addition to the enlargement/reduction processing, on the radiation images as taken in the imaging positions according to the distances between the imaging positions so that the radiation images become substantially the same in their densities, and the arithmetic means may generate the phase contrast image on the basis of the radiation images thus processed.

In accordance with a fourth aspect of the present invention, there is provided an apparatus for generating a phase contrast image on the basis of a plurality of radiation images of an object taken in imaging positions which are different from each other in the distance from the object, wherein the improvement comprises that a density correction processing means which carries out a density correction processing on the radiation images as taken in the imaging positions according to the distances between the imaging positions so that the radiation images become substantially the same in their densities, and an arithmetic means which generates the phase contrast image on the basis of the radiation images thus processed.

In accordance with the method and the apparatus of the present invention, position shift due to mismatch of the sizes of the radiation images can be prevented since an enlargement/reduction processing is carried out on the radiation images as taken in the imaging positions according to the distances between the imaging positions so that the radiation images become substantially the same in their sizes, whereby a phase contrast image can be precisely generated.

Further, since a density correction processing is carried out on the radiation images as taken in the imaging positions according to the distances between the imaging positions so that the radiation images become substantially the same in their densities, errors in a phase contrast image due to mismatch of densities of the radiation images are suppressed, whereby a phase contrast image can be precisely generated.

DESCRIPTION OF THE PREFERRED EMBODIMENTS

Figure 1:
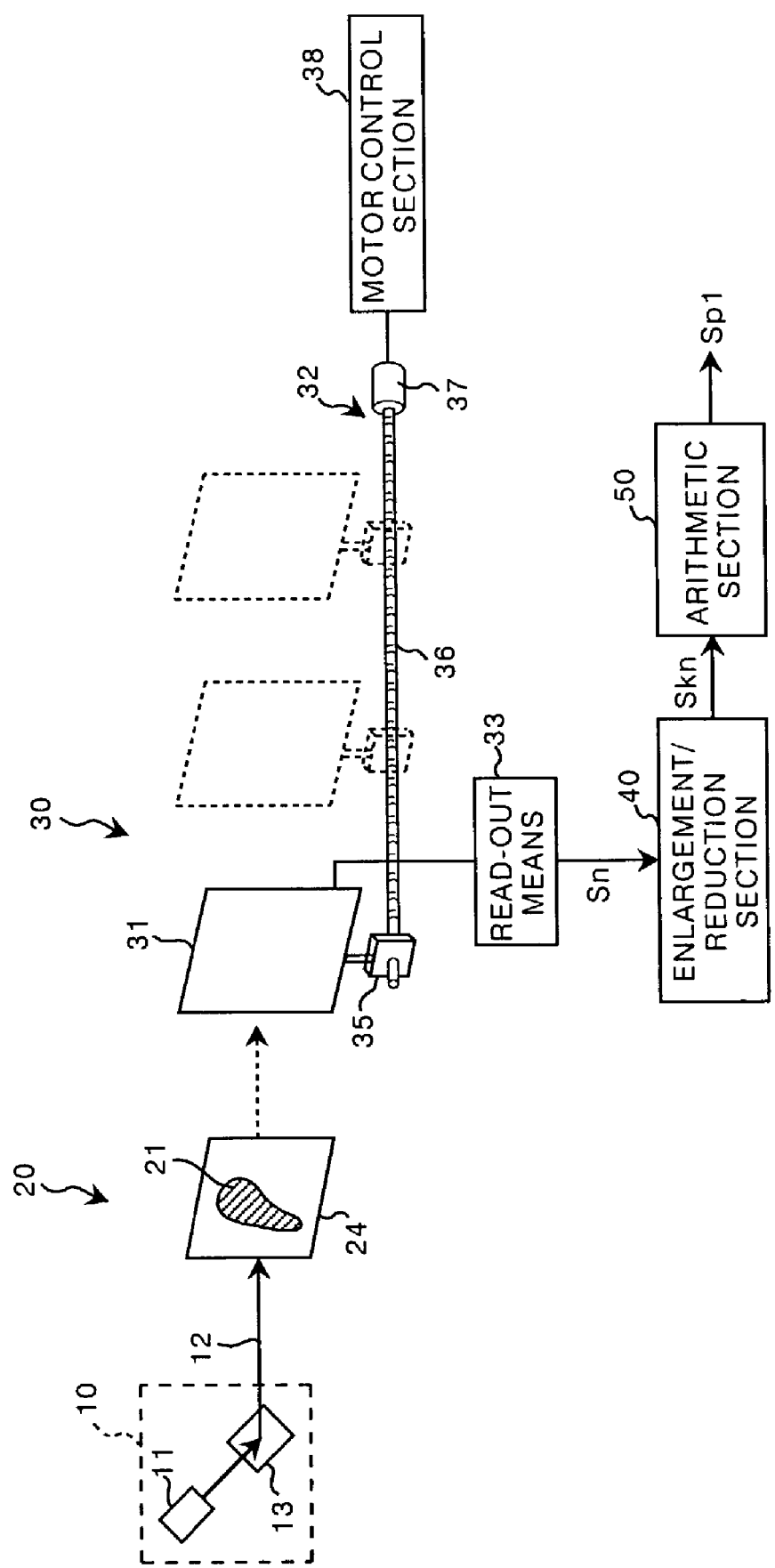
FIG. 1 is a schematic block diagram showing a phase contrast imaging apparatus in accordance with a first embodiment of the present invention.

In FIG. 1, a phase contrast imaging apparatus in accordance with a first embodiment of the present invention comprises an X-ray source section 10 which radiates an X-ray, an object support section 20 which supports an object 21, a recording section 30 which detects the X-ray passing through the object 21 at different distances from the object 21 and obtains a-plurality of pieces of image data Sn (n stands for 1 to N) representing a plurality of images of the object 21 taken at different distances, an enlargement/reduction processing section 40 which carries out an enlargement/reduction processing (to be described later) on the plurality of pieces of image data Sn and obtains a plurality of pieces of "size-matched" image data Skn and an arithmetic section 50 which obtains a phase contrast image data Sp1, representing a phase contrast image of the object 21, on the basis of the pieces of size-matched image data Skn.

The X-ray source section 10 comprises a source 11 which emits a synchrotron radiation and a crystal 13 which converts the synchrotron radiation into a monochromatic X-ray (will be simply referred to as "an X-ray"). The synchrotron radiation as emitted from the source 11 is reflected by the crystal 13 and turned into an X-ray 12.

The object support section 20 is provided with a support table 24 on which the object 21 is supported.

The recording section 30 comprises a detector panel 31 formed of a plurality of two-dimensionally arranged detecting elements, a panel moving means 32 which moves the detector panel 31 in a direction parallel to the direction of travel of the X-ray 12 passing through the object 21, and a read-out means 33 which reads out electric signals from the detecting elements of the detector panel 31 in a plurality of imaging positions set along the path of the detector panel 31 and obtains a piece of image data Sn in each of the imaging positions.

The panel moving means 32 comprises a support member 35 which is provided with a female thread and supports the detector panel 31, a threaded rod 36 which extends in a direction parallel to the direction of travel of the X-ray 12 and is provided with a male thread in mesh with the female thread of the support member 35, an electric motor 37 which rotates the threaded rod 36 about its rotating axis and a motor control section 38 which drives and stops the electric motor 37. As the motor 37 is driven by the motor control section 38, the threaded rod 36 is revolved and the detector panel 31 supported by the support member 35 is moved toward or away from the object 21 according to the direction of revolution of the threaded rod 36.

Figure 2:
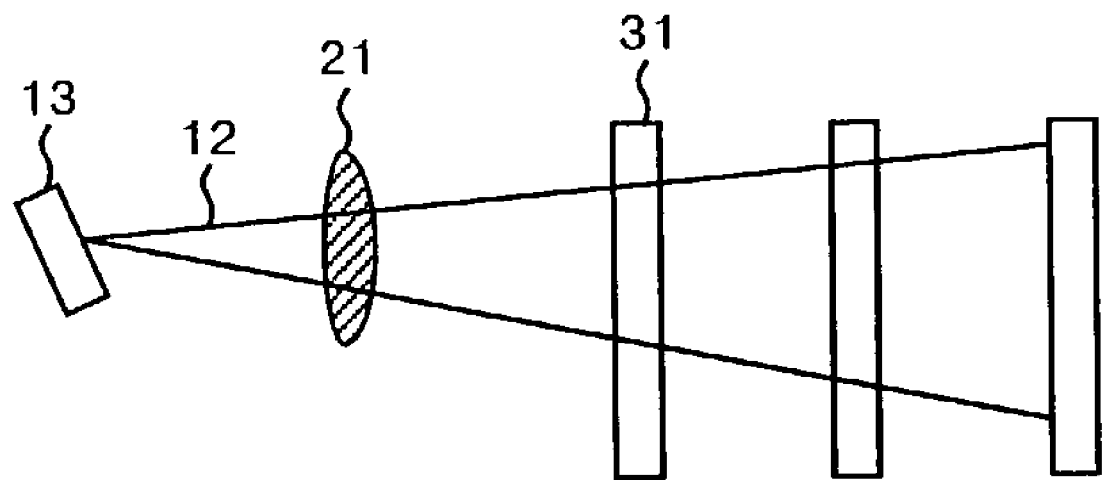
FIG. 2 is a view for illustrating propagation of an X-ray.

The enlargement/reduction processing section 40 carries out a reduction processing on the radiation images represented by pieces of image data Sn so that the radiation images represented by pieces of image data Sn become equal in size to the radiation image represented by a piece of image data S1 taken in an imaging position nearest to the object 21. That is, since the X-ray 12 is slightly divergent as shown in FIG. 2 though it is substantially parallel light, the sizes of the radiation images become slightly larger as the distance from the object 21 increases. When it is assumed that the optical axis of the X-ray 12 is on the z-axis, the imaging position nearest to the object 21 is taken as a reference imaging position where z=0, the divergent angle of the X-ray 12 is represented by θ, an imaginary origin of the divergent angle of the X-ray 12 is on a point where z=−α, and n-th imaging position is on a point where z=zn, the rate of enlargement of the radiation image obtained in n-th imaging position with respect to the radiation image obtained in the reference imaging position is (zn+α)/α. Accordingly, the enlargement/reduction section 40 carries out a reduction processing where the radiation represented by a piece of image data Sn taken in the n-th imaging position is multiplied by α/(zn+α) and obtains a processed or size-matched image data Skn. Though the image data S1 representing the image taken in the reference imaging position is not subjected to the enlargement/reduction processing, the image data S1 will be sometimes denoted by Skn for the purpose of simplicity.

Though the imaging position nearest to the object 21 is taken as the reference imaging position here, any imaging position including the imaging position farthest to the object 21 may be taken as the reference imaging position. In this case, the radiation (X-ray) image taken in each of the imaging positions is enlarged or reduced according to whether the imaging position is nearer or further to the object 21 than the reference imaging position.

The arithmetic section 50 calculates image data Sp1 representing a phase contrast image on the basis of the pieces of image data Sn by a method described in the aforesaid paper 1. The method will be described, hereinbelow. It is assumed that the transmittance of the object is represented by the following formula (1).

$$T(x, y) = A(x, y)e^{i\psi(x, y)} \tag{1}$$

wherein $T(x, y)$ represents a transmittance function, $A(x, y)$ represents a transmittance intensity function, $\psi(x, y)$ represents a phase shift function and $(x, y)$ represents the coordinates representing the position on the detector panel 31.

When the object is a thin object whose transmittance intensity is negligible, that is, $A(x, y)$ is substantially 1, the spatial frequency component of the phase shift is calculated by the use of the spatial frequency components $I_{dn}(fx, fy)$ obtained by Fourier transform of images $I_{dn}(x, y)$ taken at the distances dn (n=1 to N) between the object 21 and the detector panel 31 as represented by the following formula (2). In each of the images $I_{dn}(x, y)$, the values of pixels are given by the values of pixels in the positions represented by $(x, y)$ of the image data Sn taken at the distances dn.

$$\psi(fx, fy \neq 0) = \frac{\sum_{n=1\cdots N} \exp(i\pi\lambda dnf^2) Idn(fx, fy)}{N - \sum_{n=1\cdots N} \exp(2i\pi\lambda dnf^2)} \tag{2}$$

wherein N represents the number of pieces of image data Sn, f represents the spatial frequency, $\psi(fx, fy \neq 0)$ represents the frequency component of the phase shift when the frequency is not 0, and $I_{dn}(fx, fy)$ represents the spatial frequency component of $I_{dn}(x,y)$.

By inverse Fourier transform of the spatial frequency component of the phase shift, the phase shift, i.e., the phase difference $\psi(x,y)$ can be calculated. Since the phase difference $\psi(x,y)$ takes a value in the range of from 0 to $2\pi$, image data Sp1 representing the phase contrast image can be obtained by allocating the calculated phase difference $\psi(x,y)$ to, for instance, values of 8 bits.

Though it is assumed here that the object is a thin object whose transmittance intensity is negligible, that is, $A(x,y)$ is substantially 1, the phase shift can be calculated also for thick objects by the use of a similar algorithm.

Figure 3:
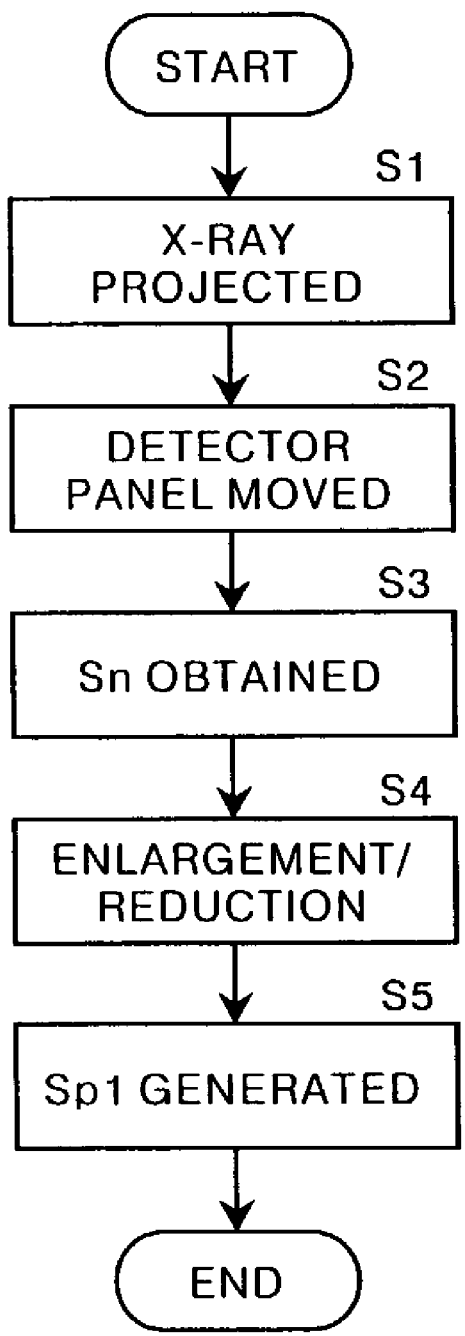
FIG. 3 is a flow chart for illustrating the operation of the phase contrast imaging apparatus of the first embodiment.

The operation of the phase contrast imaging apparatus of the first embodiment of the present invention will be described, hereinbelow, with reference to the flow chart shown in FIG. 3. The source 11 is driven to emit a synchrotron radiation and the synchrotron radiation is reflected by the crystal 13 and is converted into a monochromatic X-ray 12. The X-ray 12 is projected onto the object 21. (step S1) Then the control section 38 drives the motor 37 to move the detector panel 31 away from the object 21 from the initial position nearest to the object 21. (step S2) As the detector panel 31 is moved, radiation images of the object 21 recorded on the detector panel 31 in the respective imaging positions as electric charges of the detecting elements of the detector panel 31 are read out by the read-out means 33 and a plurality of pieces of image data Sn representing the radiation images are obtained. (step S3)

The pieces of image data Sn obtained are input into the enlargement/reduction processing section 40 and are subjected to the enlargement/reduction processing, whereby a plurality of pieces of size-matched image data Skn are obtained. (step S4)

The pieces of size-matched image data Skn are input into the arithmetic section 50 and the arithmetic section 50 generates phase contrast image data Sp1 representing a phase contrast image on the basis of a plurality of pieces of size-matched image data Skn in the manner described above. (step S5) An image based on the phase contrast image data is reproduced on a monitor or output as a print.

As can be understood from the description above, in the phase contrast imaging apparatus of this embodiment, position shift due to mismatch of the sizes of the radiation images represented by image data Sn can be prevented since an enlargement/reduction processing is carried out on the radiation images represented by the image data Sn according to the distances between the imaging positions so that the radiation images become substantially the same in their sizes, whereby a phase contrast image can be precisely generated.

Figure 4:
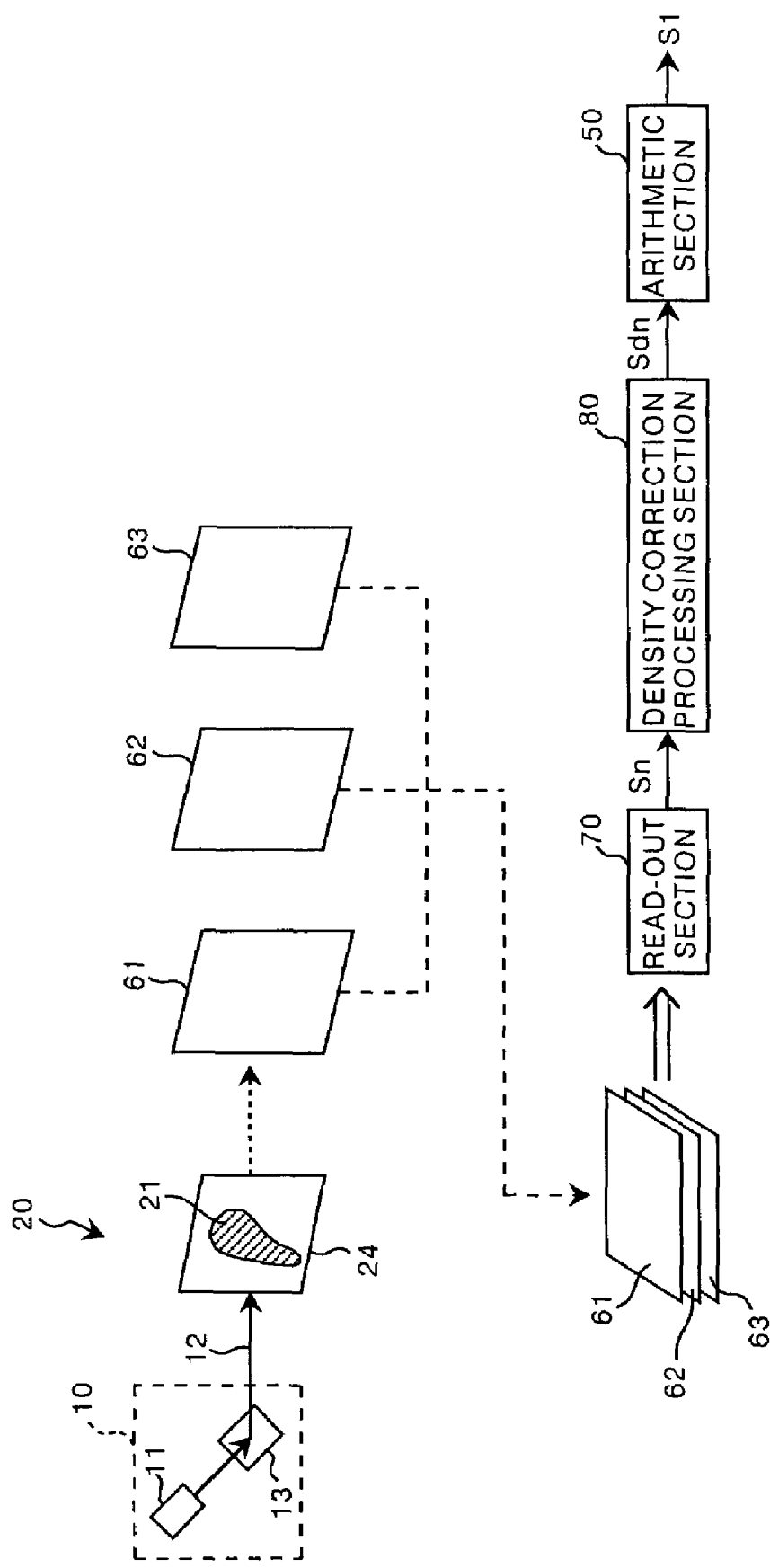
FIG. 4 is a schematic block diagram showing a phase contrast imaging apparatus in accordance with a second embodiment of the present invention.
Figure 5:
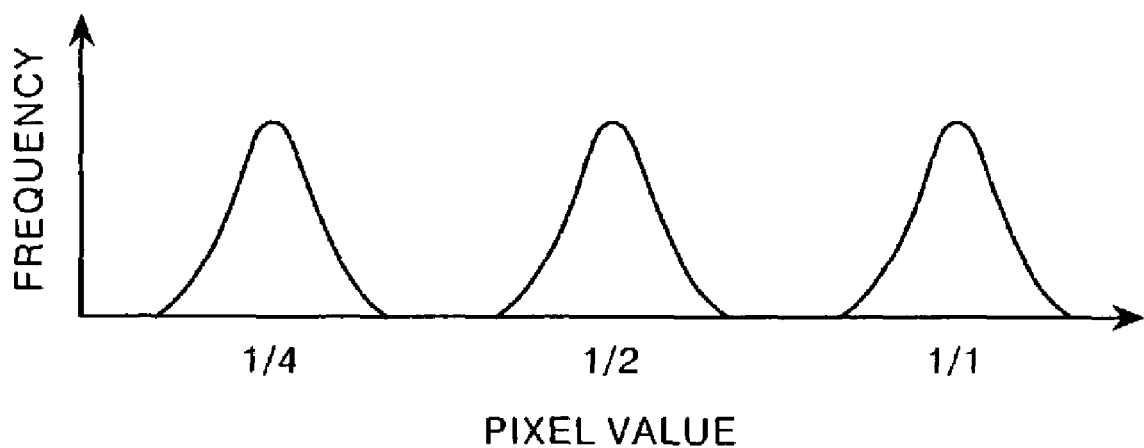
FIG. 5 is a view for illustrating the density shift.
Figure 6:
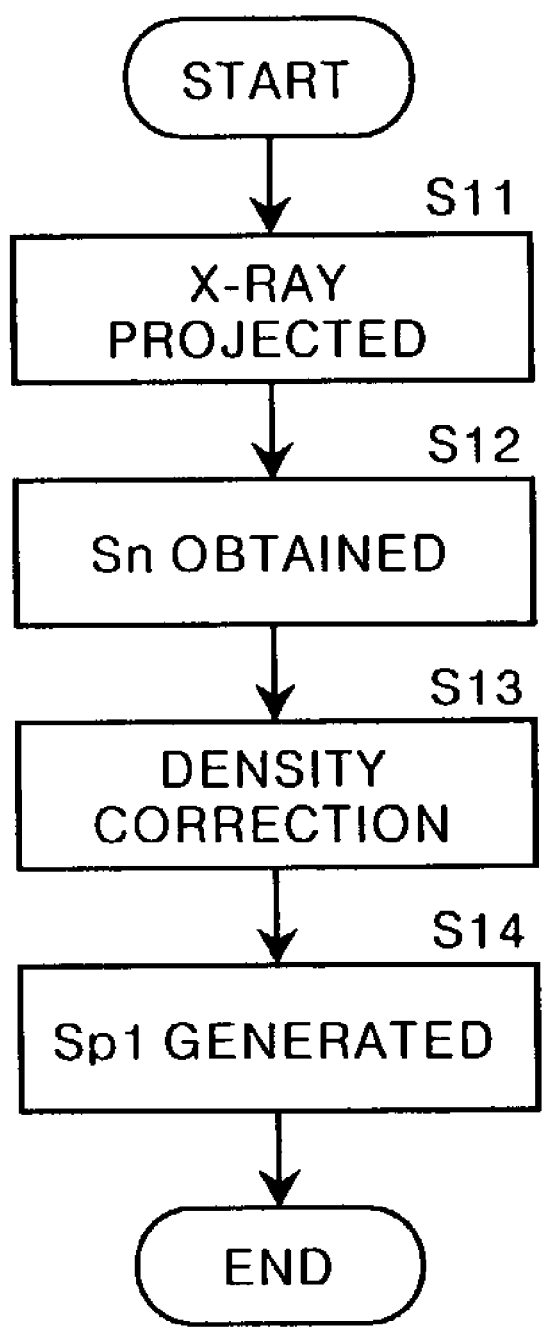
FIG. 6 is a flow chart for illustrating the operation of the phase contrast imaging apparatus of the second embodiment.

A phase contrast imaging apparatus in accordance with a second embodiment of the present invention will be described with reference to FIGS. 4 to 6, hereinbelow. In FIG. 4, the elements analogous to those shown in FIG. 1 are given the same reference numerals and will not be described here. The phase contrast imaging apparatus of the second embodiment differs from that of the first embodiment in that a plurality of (three in this particular embodiment) stimulable phosphor sheets 61, 62 and 63 are set in respective imaging positions so that three pieces of image data Sn are obtained at one time instead of moving a single detector panel 31 from imaging position to imaging position so that three pieces of image data Sn are obtained in three steps, and that a density correction processing section 80 which carries out a density correction processing on the three pieces of image data Sn obtained in different imaging positions and obtains a plurality of density-matched image data Sdn is provided in place of the enlargement/reduction processing section 40.

When X-ray images are recorded on the stimulable phosphor sheets 61, 62 and 63, stimulating light is projected onto the stimulable phosphor sheets 61, 62, and 63 and a read-out section photoelectrically reads stimulated emission emitted from the stimulable phosphor sheets upon exposure to the stimulating light, whereby a plurality of pieces of image data Sn representing X-ray images are obtained.

The density correction processing section 80 carries out a density correction processing on the radiation images represented by pieces of image data Sn so that the radiation images represented by pieces of image data Sn become equal in density to the radiation image represented by a piece of image data S1 taken in an imaging position nearest to the object 21. That is, when a plurality of X-ray images are to be taken at one time by exposing a plurality of stimulable phosphor sheets disposed in the respective imaging positions to an X-ray 12 passing through the object 21, the X-ray 12 is attenuated each time it passes through a stimulable phosphor sheet, and the density (e.g., an average density or an intermediate density) of an X-ray image taken in a given imaging position is reduced in proportion to the number of the stimulable phosphor sheets which the X-ray 12 passes through before. Since image data Sn is generally obtained by a logarithmic transformation of the amount of stimulated emission emitted from each of the stimulable phosphor sheets 61, 62 and 63, when the stimulable phosphor sheets 61, 62 and 63 are of a thickness such as to cut by half the intensity of the X-ray 12 passing therethrough, each image data Sn will provide a histogram as shown in FIG. 5. In FIG. 5, the abscissa represents a pixel value (a logarithmic value) of an X-ray image represented by each piece of image data Sn, and $1/1$, $1/2$ and $1/4$ respectively denotes the positions of the peak of the histogram for the pieces of image data S1, S2 and S3 obtained through the stimulable phosphor sheets 61, 62 and 63 which are nearer to the object 21 in this order. As can be seen from FIG. 5, the X-ray image represented by each piece of image data Sn is obtained by shifting the density of the X-ray image represented by another piece of image data Sn.

Accordingly, the density correction processing section 80 shifts the densities of the X-ray images so that the X-ray images represented by pieces of image data Sn become equal in density to a reference X-ray image (e.g., the X-ray image represented by an image data S1 obtained from the stimulable phosphor sheet 61 nearest to the object 21). The amount of shift of density may be determined in advance by creating histograms for pieces of image data obtained when the stimulable phosphor sheets 61, 62 and 63 are exposed to the X-ray 12 without the object 21 and calculating the amounts of shift of density which will conform the signal values of the peaks of the histograms with each other.

The operation of the phase contrast imaging apparatus of the second embodiment of the present invention will be described, hereinbelow, with reference to the flow chart shown in FIG. 6. The source 11 is driven to emit a synchrotron radiation and the synchrotron radiation is reflected by the crystal 13 and is converted into a monochromatic X-ray 12. The X-ray 12 is projected onto the object 21. (step S11) BY thus projecting the X-ray 12 onto the object 21, X-ray images of the object 21 are recorded on the respective stimulable phosphor sheets 61, 62 and 63 in the respective imaging positions. The read-out section 70 reads out the X-ray images from the stimulable phosphor sheets 61, 62 and 63 and obtains three pieces of image data Sn representing the X-ray images. (step S12)

The pieces of image data Sn obtained are input into the density correction processing section 80 and are subjected to the density correction processing, whereby a plurality of pieces of density-matched image data Sdn are obtained. (step S13)

The pieces of density-matched image data Sdn are input into the arithmetic section 50 and the arithmetic section 50 generates phase contrast image data Sp1 representing a phase contrast image on the basis of a plurality of pieces of density-matched image data Sdn in the manner described above. (step S14).

As can be understood from the description above, in the phase contrast imaging apparatus of this embodiment, since a density correction processing is carried out on the X-ray images as taken in the imaging positions according to the distances between the imaging positions so that the X-ray images become substantially the same in their densities, errors in a phase contrast image due to mismatch of densities of the X-ray images are suppressed, whereby a phase contrast image can be precisely generated.

Figure 7:
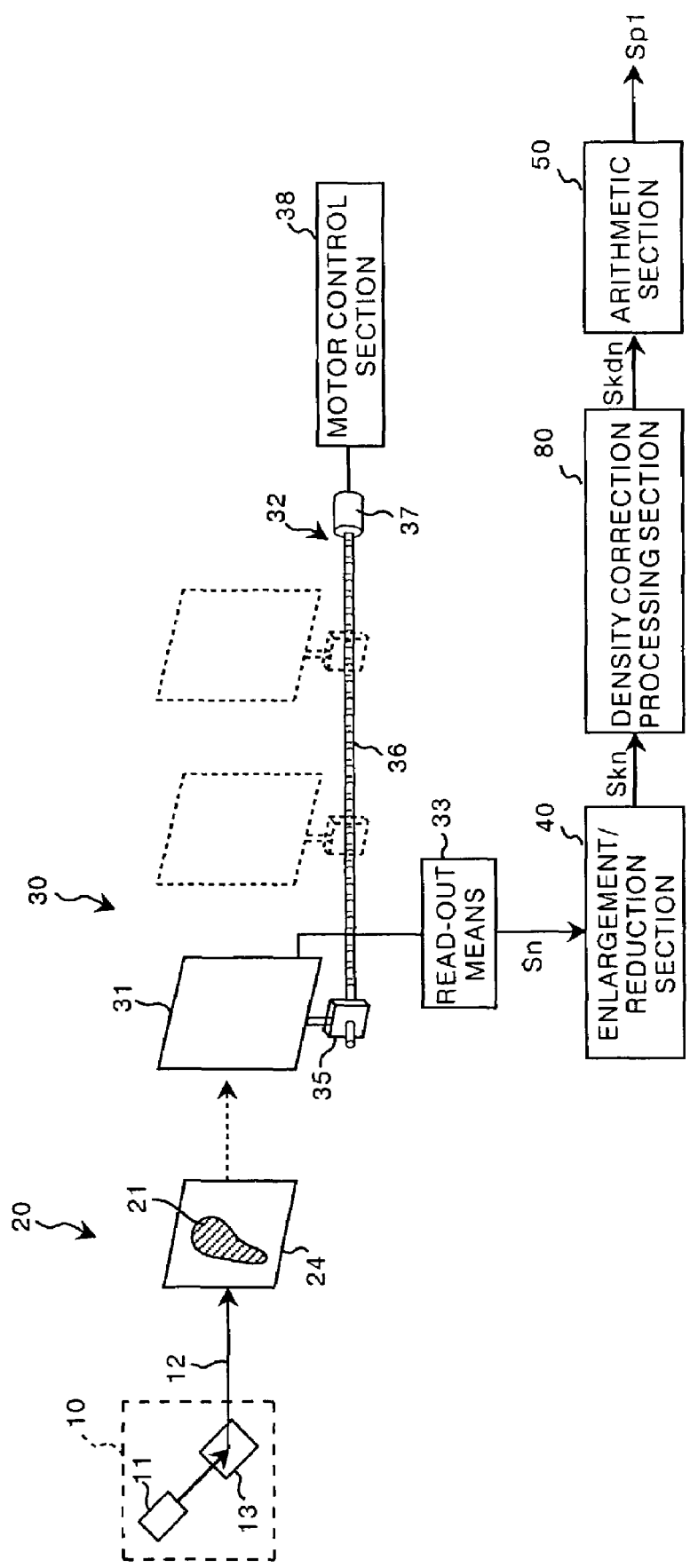
FIG. 7 is a schematic block diagram showing a phase contrast imaging apparatus in accordance with a third embodiment of the present invention.
Figure 8:
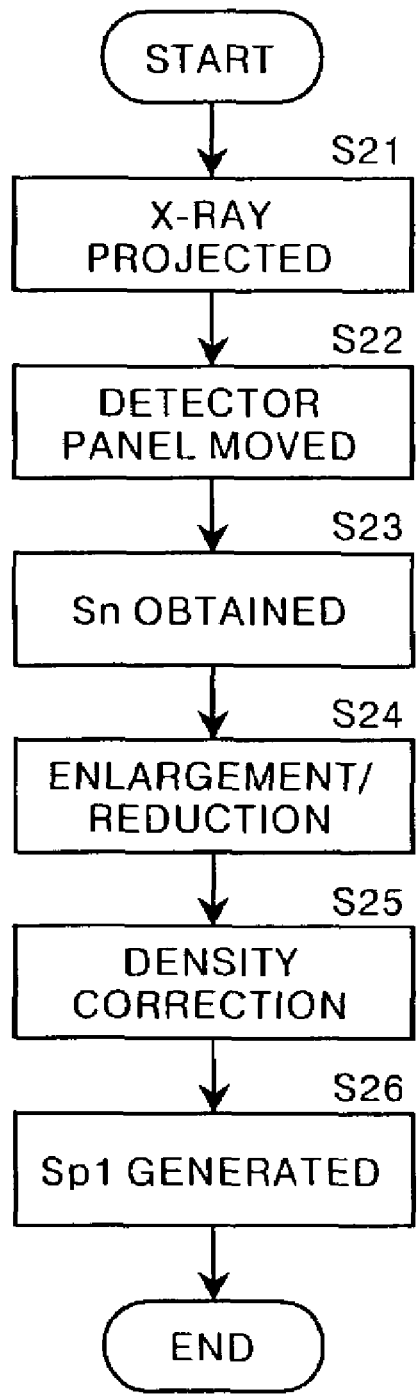
FIG. 8 is a flow chart for illustrating the operation of the phase contrast imaging apparatus of the third embodiment.

A phase contrast imaging apparatus in accordance with a third embodiment of the present invention will be described with reference to FIGS. 7 and 8, hereinbelow. In FIG. 7, the elements analogous to those shown in FIG. 1 are given the same reference numerals and will not be described here. The phase contrast imaging apparatus of the third embodiment differs from that of the first embodiment in that a plurality of pieces of image data Sn is subjected to the enlargement/reduction processing into a plurality of pieces of size-matched image data Skn, the plurality of size-matched image data Skn is further subjected to a density correction processing by a density correction processing section 80 into a plurality of size/density-matched image data Skdn, and an image data Sp1 representing a phase contrast image is generated on the basis of the plurality of size/density-matched image data Skdn.

As described above, the size of the X-ray image obtained increases as the distance of the imaging position from the object 21 increases. However as the size of the X-ray image obtained increases, the density of the X-ray 12 projected onto the detector panel 31 is lowered, that is, the amount of the X-ray 12 impinging upon the detector panel 31 per unit area is reduced. In the third embodiment, by further carrying out the density correction processing on the plurality of pieces of image data Sn after they are subjected to the enlargement/reduction processing, the radiation images as taken in the imaging positions are made substantially the same both in their sizes and densities. The enlargement/reduction processing and the density correction processing may be carried out in similar manners to those in the first and second embodiments described above.

The operation of the phase contrast imaging apparatus of the third embodiment of the present invention will be described, hereinbelow, with reference to the flow chart shown in FIG. 8. The source 11 is driven to emit a synchrotron radiation and the synchrotron radiation is reflected by the crystal 13 and is converted into a monochromatic X-ray 12. The X-ray 12 is projected onto the object 21. (step S21) Then the control section 38 drives the motor 37 to move the detector panel 31 away from the object 21 from the initial position nearest to the object 21. (step S22) As the detector panel 31 is moved, radiation images of the object 21 recorded on the detector panel 31 in the respective imaging positions as electric charges of the detecting elements of the detector panel 31 are read out by the read-out means 33 and a plurality of pieces of image data Sn representing the radiation images are obtained. (step S23).

The pieces of image data Sn obtained are input into the enlargement/reduction processing section 40 and are subjected to the enlargement/reduction processing, whereby a plurality of pieces of size-matched image data Skn are obtained. (step S24) The plurality of size-matched image data Skn are further input into the density correction processing section 80 and are subjected to the density correction processing, whereby a plurality of pieces of size/density-matched image data Skdn are obtained. (step S25) The pieces of size/density-matched image data Skdn are further input into the arithmetic section 50 and the arithmetic section 50 generates phase contrast image data Sp1 representing a phase contrast image on the basis of a plurality of pieces of size/density-matched image data Skdn in the manner described above. (step S26).

As can be understood from the description above, in the phase contrast imaging apparatus of this embodiment, since the enlargement-reduction processing and the density correction processing are carried out on the X-ray images as taken in the imaging positions according to the distances between the imaging positions so that the X-ray images become substantially the same in their sizes and densities, errors in a phase contrast image due to position shift and mismatch of densities of the X-ray images are suppressed, whereby a phase contrast image can be precisely generated.

Though, in the third embodiment, the enlargement/reduction processing is carried out before the density correction processing, the latter may be carried out before the former.

Though, in the first and third embodiments, a plurality of X-ray images are taken in a plurality of imaging positions by moving a single detector panel 31 in a direction parallel to the direction of travel of the X-ray 12, a plurality of X-ray images may be taken at one time by disposing a plurality of detector panels (e.g., stimulable phosphor sheets 61, 62 and 63) in the respective imaging positions as in the second embodiment.

Further, though, in the second embodiment, a plurality of X-ray images are taken at one time by disposing a plurality of detector panels (e.g., stimulable phosphor sheets 61, 62 and 63) in the respective imaging positions, a plurality of X-ray images may be taken in a plurality of imaging positions by moving a single detector panel 31 in a direction parallel to the direction of travel of the X-ray 12 as in the first and third embodiments.

Further, the source of the X-ray 12 need not be limited to those emitting a synchrotron radiation. The X-ray 12 need not be limited to a monochromatic X-ray.

Further, though, in the embodiments described above, an X-ray is employed as the radiation, a radiation other than X-ray, e.g., α-ray, β-ray, γ-ray, an electron beam or an ultraviolet ray, may be employed.

A computer program for causing a computer to perform the method of the present invention may be recorded in a computer readable medium so that the computer can perform the method when loaded with the recording medium. A skilled artisan would know that the computer readable medium is not limited to any specific type of storage devices and includes any kind of device, including but not limited to CDs, floppy disks, RAMs, ROMs, hard disks, magnetic tapes and internet downloads, in which computer instructions can be stored and/or transmitted. Transmission of the computer code through a network or through wireless transmission means is also within the scope of this invention. Additionally, computer code/instructions include, but are not limited to, source, object and executable code and can be in any language including higher level languages, assembly language and machine language.

What is claimed is:

1. A method of generating a phase contrast image on the basis of a plurality of radiation images of an object taken in imaging positions which are different from each other in the distance from the object, wherein an improvement comprises that at least one of an enlargement and reduction processing is carried out on the radiation images as taken in the imaging positions according to the distances between the imaging positions so that the radiation images become substantially the same in their sizes, and a phase contrast image is generated on the basis of the radiation images thus processed, wherein the phase contrast image represents a phase shift amount according to the plurality of radiation images, and the phase contrast image is generated by performing spatial frequency conversion on each of the plurality of radiation images on which the at least one of the enlargement and the reduction processing has been performed, by obtaining a phase shift amount by calculation using a spatial frequency component of each of the plurality of radiation images, on which the spatial frequency conversion has been performed, and by generating an image based on the obtained phase shift amount.

2. A method as defined in claim 1 in which a density correction processing is further carried out, in addition to the at least one of the enlargement and reduction processing, on the radiation images as taken in the imaging positions according to the distances between the imaging positions so that the radiation images become substantially the same in their densities, and a phase contrast image is generated on the basis of the radiation images thus processed.

3. The method of claim 1, further comprising providing a plurality of detector panels for respectively capturing the plurality of radiation images.

4. The method of claim 3, wherein the plurality of radiation images, which are respectively captured on the plurality of detector panels, are taken at a same time.

5. The method of claim 1, wherein the at least one of the enlargement and reduction processing uses a size of one of the plurality of radiation images as a reference size when enlarging/reducing the plurality of images.

6. The method of claim 1, wherein the phase contrast image represents a phase shift, due to propagation, of a wave of radiation used to generate the radiation images of the object.

7. The method of claim 6, wherein the phase shift ranges from 0 to $2\pi$.

8. The method of claim 1, further comprising providing a detector panel, which is moved to the respective imaging locations when capturing the plurality of radiation images.

9. A method of generating a phase contrast image on the basis of a plurality of radiation images of an object taken in imaging positions which are different from each other in the distance from the object, wherein an improvement comprises that a density correction processing is carried out on the radiation images as taken in the imaging positions according to the distances between the imaging positions so that the radiation images become substantially the same in their densities, and a phase contrast image is generated on the basis of the radiation images thus processed, and wherein the phase contrast image is generated by performing spatial frequency conversion on each of the plurality of radiation images on which the at least one of the enlargement and the reduction processing has been performed, by obtaining a phase shift amount by calculation using a spatial frequency component of each of the plurality of radiation images, on which the spatial frequency conversion has been performed, and by generating an image based on the obtained phase shift amount.

10. The method of claim 9, further comprising providing a plurality of detector panels for respectively capturing the plurality of radiation images.

11. The method of claim 10, wherein the plurality of radiation images, which are respectively captured on the plurality of detector panels, are taken at a same time.

12. The method of claim 9, wherein the density correction processing uses a density of one of the plurality of radiation images as a reference density when correcting density on the plurality of images.

13. The method of claim 9, wherein the phase contrast image represents a phase shift, due to propagation, of a wave of radiation used to generate the radiation images of the object.

14. The method of claim 13, wherein the phase shift ranges from 0 to $2\pi$.

15. The method of claim 9, further comprising providing a detector panel, which is moved to the respective imaging locations when capturing the plurality of radiation images.

16. An apparatus for generating a phase contrast image on the basis of a plurality of radiation images of an object taken in imaging positions which are different from each other in the distance from the object, wherein an improvement comprises least one of an enlargement and reduction processing means which carries out least one of an enlargement and reduction processing on the radiation images as taken in the imaging positions according to the distances between the imaging positions so that the radiation images become substantially the same in their sizes, and an arithmetic means which generates a phase contrast image on the basis of the radiation images thus processed, wherein the phase contrast image represents a phase shift amount according to the plurality of radiation images, and the arithmetic means which generates the phase contrast image is a means for generating the phase contrast image by performing spatial frequency conversion on each of the plurality of radiation images on which the at least one of the enlargement and reduction processing has been performed, by obtaining a phase shift amount by calculation using a spatial frequency component of each of the plurality of radiation images, on which the spatial frequency conversion has been performed, and by generating an image based on the obtained phase shift amount.

17. The apparatus as defined in claim 16 which further comprises a density correction processing means which carries out a density correction processing, in addition to the at least one of the enlargement and reduction processing, on the radiation images as taken in the imaging positions according to the distances between the imaging positions so that the radiation images become substantially the same in their densities, and in which the arithmetic means generates a phase contrast image on the basis of the radiation images thus processed.

18. The apparatus of claim 16, further comprising a plurality of detector panels for respectively capturing the plurality of radiation images.

19. The apparatus of claim 18, wherein the plurality of radiation images, which are respectively captured on the plurality of detector panels, are taken at a same time.

20. The apparatus of claim 16, wherein the at least one of the enlargement and reduction processing means uses a size of one of the plurality of radiation images as a reference size when enlarging/reducing the plurality of images.

21. The apparatus of claim 16, wherein the phase contrast image represents a phase shift, due to propagation, of a wave of radiation used to generate the radiation images of the object.

22. The apparatus of claim 21, wherein the phase shift ranges from 0 to $0\pi$.

23. The apparatus of claim 16, further comprising a detector panel, which is moved to the respective imaging locations when capturing the plurality of radiation images.

24. An apparatus for generating a phase contrast image on the basis of a plurality of radiation images of an object taken in imaging positions which are different from each other in the distance from the object, wherein an improvement comprises that a density correction processing means which carries out a density correction processing on the radiation images as taken in the imaging positions according to the distances between the imaging positions so that the radiation images become substantially the same in their densities, and an arithmetic means which generates a phase contrast image on the basis of the radiation images thus processed, wherein the arithmetic means which generates the phase contrast image is a means for generating the phase contrast image by performing spatial frequency conversion on each of the plurality of radiation images on which the at least one of the enlargement and reduction processing has been performed, by obtaining a phase shift amount by calculation using a spatial frequency component of each of the plurality of radiation images, on which the spatial frequency conversion has been performed, and by generating an image based on the obtained phase shift amount.

25. The apparatus of claim 24, further comprising a plurality of detector panels for respectively capturing the plurality of radiation images.

26. The apparatus of claim 25, wherein the plurality of radiation images, which are respectively captured on the plurality of detector panels, are taken at a same time.

27. The apparatus of claim 24, wherein the density correction processing means uses a density of one of the plurality of radiation images as a reference density when correcting density on the plurality of images.

28. The apparatus of claim 24, wherein the phase contrast image represents a phase shift, due to propagation, of a wave of radiation used to generate the radiation images of the object.

29. The apparatus of claim 28, wherein the phase shift ranges from 0 to $0\pi$.

30. The apparatus of claim 24, further comprising a detector panel, which is moved to the respective imaging locations when capturing the plurality of radiation images.

31. A computer readable medium storing a computer program for causing a computer to perform a procedure of generating a phase contrast image on the basis of a plurality of radiation images of an object taken in imaging positions which are different from each other in the distance from the object comprising at least one of an enlargement and reduction processing step which is carried out on the radiation images as taken in the imaging positions according to the distances between the imaging positions so that the radiation images become substantially the same in their sizes, and a phase contrast image generation step of generating a phase contrast image on the basis of the radiation images thus processed, wherein the phase contrast image represents a phase shift amount according to the plurality of radiation images, and the phase contrast image is generated by performing spatial frequency conversion on each of the plurality of radiation images on which the at least one of the enlargement and the reduction processing has been performed, by obtaining a phase shift amount by calculation using a spatial frequency component of each of the plurality of radiation images, on which the spatial frequency conversion has been performed, and by generating an image based on the obtained phase shift amount.

32. A computer readable medium storing a computer program as defined in claim 31 in which the procedure further comprising a density correction processing step which is further carried out, in addition to the at least one of the enlargement and reduction processing, on the radiation images as taken in the imaging positions according to the distances between the imaging positions so that the radiation images become substantially the same in their densities, and a phase contrast image generation step of generating a phase contrast image on the basis of the radiation images thus processed.

33. The computer readable medium of claim 31, wherein a plurality of detector panels are provided for respectively capturing the plurality of radiation images.

34. The computer readable medium of claim 33, wherein the plurality of radiation images, which are respectively captured on the plurality of detector panels, are taken at a same time.

35. The computer readable medium of claim 31, wherein the at least one of the enlargement and reduction processing step uses a size of one of the plurality of radiation images as a reference size when enlarging/reducing the plurality of images.

36. The computer readable medium of claim 31, wherein the phase contrast image represents a phase shift, due to propagation, of a wave of radiation used to generate the radiation images of the object.

37. The computer readable medium of claim 36, wherein the phase shift ranges from 0 to $2\pi$.

38. The computer readable medium of claim 31, wherein a detector panel is moved to the respective imaging locations when capturing the plurality of radiation images.

39. A computer readable medium storing a computer program for causing a computer to perform a procedure of generating a phase contrast image on the basis of a plurality of radiation images of an object taken in imaging positions which are different from each other in the distance from the object comprising a density correction processing step which is carried out on the radiation images as taken in the imaging positions according to the distances between the imaging positions so that the radiation images become substantially the same in their densities, and a phase contrast image generating step of generating a phase contrast image on the basis of the radiation images thus processed, wherein the phase contrast image represents a phase shift amount according to the plurality of radiation images, and the phase contrast image is generated by performing spatial frequency conversion on each of the plurality of radiation images on which the at least one of the enlargement and the reduction processing has been performed, by obtaining a phase shift amount by calculation using a spatial frequency component of each of the plurality of radiation images, on which the spatial frequency conversion has been performed, and by generating an image based on the obtained phase shift amount.

40. The computer readable medium of claim 39, wherein a plurality of detector panels are provided for respectively capturing the plurality of radiation images.

41. The computer readable medium of claim 40, wherein the plurality of radiation images, which are respectively captured on the plurality of detector panels, are taken at a same time.

42. The computer readable medium of claim 39, wherein the density correction processing step uses a density of one of the plurality of radiation images as a reference density when correcting density on the plurality of images.

43. The computer readable medium of claim 39, wherein the phase contrast image represents a phase shift, due to propagation, of a wave of radiation used to generate the radiation images of the object.

44. The computer readable medium of claim 43, wherein the phase shift ranges from 0 to $2\pi$.

45. The computer readable medium of claim 39, wherein a detector panel is moved to the respective imaging locations when capturing the plurality of radiation images.

* * * * *